US 6,644,365 B1

(12) United States Patent
Spero et al.

(10) Patent No.: US 6,644,365 B1
(45) Date of Patent: Nov. 11, 2003

(54) TILTING DIRECT DUAL FILLING DEVICE

(75) Inventors: Richard Spero, Brentwood, CA (US);
Adam Hagmann, Brentwood, CA (US)

(73) Assignees: Baxter International, Inc., Deerfield, IL (US); Baxter Healthcare SA, Kanton Zurich (CH)

( * ) Notice: Subject to any disclaimer, the term of this patent is extended or adjusted under 35 U.S.C. 154(b) by 0 days.

(21) Appl. No.: 10/126,789

(22) Filed: Apr. 19, 2002

(51) Int. Cl.⁷ .................................................. B65B 3/04
(52) U.S. Cl. .......................... 141/318; 141/18; 141/25; 141/26; 141/27; 141/386
(58) Field of Search .............................. 141/2, 18, 20.5, 141/21–23, 25–27, 318–320, 383, 386

(56) References Cited

U.S. PATENT DOCUMENTS

| | | | |
|---|---|---|---|
| 766,202 A | * | 8/1904 | Vandewater ................. 141/318 |
| 2,122,722 A | | 7/1938 | O'Neil |
| 3,134,407 A | * | 5/1964 | Wegman ....................... 141/18 |
| 3,405,706 A | | 10/1968 | Cinqualbre |
| 3,767,085 A | | 10/1973 | Cannon et al. |
| 3,776,700 A | | 12/1973 | Gallant |
| 3,807,467 A | | 4/1974 | Tascher et al. |
| 3,833,030 A | | 9/1974 | Waldbauer, Jr. et al. |
| 4,128,098 A | | 12/1978 | Bloom et al. |
| 4,325,913 A | | 4/1982 | Wardlaw |
| 4,359,049 A | | 11/1982 | Redl et al. |
| 4,434,820 A | | 3/1984 | Glass |
| 4,552,277 A | | 11/1985 | Richardson et al. |
| 4,629,455 A | | 12/1986 | Kanno |
| 4,690,165 A | | 9/1987 | Leytes et al. |
| 4,810,123 A | * | 3/1989 | Bruggeman ................. 401/144 |
| 4,856,567 A | | 8/1989 | Cosmai |
| 4,883,483 A | | 11/1989 | Lindmayer |
| 4,902,281 A | | 2/1990 | Avoy |
| 4,969,669 A | | 11/1990 | Sauer |
| 4,978,336 A | | 12/1990 | Capozzi et al. |

(List continued on next page.)

FOREIGN PATENT DOCUMENTS

| | | |
|---|---|---|
| EP | 0156098 A2 | 12/1984 |
| EP | 0 302 411 B1 | 6/1992 |
| EP | 0302411 B1 | 6/1992 |
| EP | 0 738 498 A1 | 10/1996 |
| EP | 0738498 A1 | 10/1996 |
| EP | 0 156 098 B1 | 11/1998 |
| WO | WO 89/04676 | 6/1989 |
| WO | WO 90/01959 | 3/1990 |
| WO | WO 94/06487 | 3/1994 |
| WO | WO 96/29113 A1 | 9/1996 |
| WO | WO97/25015 | 7/1997 |
| WO | WO 97/28834 A1 | 8/1997 |
| WO | WO 98/07846 A1 | 2/1998 |
| WO | WO 98/46300 A1 | 10/1998 |
| WO | WO 99/17833 A1 | 4/1999 |
| WO | WO 99/30769 | 6/1999 |
| WO | WO 99/32155 | 7/1999 |
| WO | WO 99/39642 A1 | 8/1999 |
| WO | WO 99/62588 A1 | 12/1999 |

*Primary Examiner*—J. Casimer Jacyna
(74) *Attorney, Agent, or Firm*—Stradling Yocca Carlson & Rauth

(57) ABSTRACT

A direct dual filling device for sealing agents capable of transferring a material from a commercially available material container to a material applicator. The filling device of the present invention comprises a hood defining at least one receiving aperture, an applicator interface in communication with the hood and having at least one filling port formed thereon, at least one transfer conduit in communication with the at least one filling port, at least one withdrawal cannula located within the receiving aperture and in communication with the at least one transfer conduit, and a container support device capable of receiving and supporting at least one material container in an upright tilted position within the receiving aperture. The hood may include at least one engaging surface and at least one displacement recess. In addition, the container support device may include at least one biasing member capable of biasing the material container from an upright position to an upright tilted position, thereby enabling the withdrawal of substantially all the material from the material container.

18 Claims, 9 Drawing Sheets

U.S. PATENT DOCUMENTS

| | | | |
|---|---|---|---|
| 5,116,315 A | 5/1992 | Capozzi et al. | |
| 5,163,433 A | 11/1992 | Kagawa et al. | |
| 5,171,146 A | 12/1992 | Guerci | |
| 5,171,214 A | 12/1992 | Kolber et al. | |
| 5,195,985 A | 3/1993 | Hall | |
| 5,226,877 A | 7/1993 | Epstein | |
| 5,240,146 A | 8/1993 | Smedley et al. | |
| 5,247,972 A * | 9/1993 | Tetreault | 141/27 |
| 5,297,561 A | 3/1994 | Hulon | |
| 5,329,976 A | 7/1994 | Haber et al. | |
| 5,368,563 A | 11/1994 | Lonneman et al. | |
| 5,405,607 A | 4/1995 | Epstein | |
| 5,445,631 A | 8/1995 | Uchida | |
| 5,454,409 A | 10/1995 | McAffer et al. | |
| 5,468,233 A * | 11/1995 | Schraga | 604/207 |
| 5,478,323 A | 12/1995 | Westwood et al. | |
| 5,487,738 A * | 1/1996 | Sciulli | 604/414 |
| 5,542,760 A | 8/1996 | Chanoch et al. | |
| 5,566,729 A * | 10/1996 | Grabenkort et al. | 141/25 |
| 5,582,596 A | 12/1996 | Fukunaga et al. | |
| 5,585,007 A | 12/1996 | Antanavich et al. | |
| 5,591,143 A | 1/1997 | Trombley, III et al. | |
| 5,605,255 A | 2/1997 | Reidel et al. | |
| 5,605,541 A | 2/1997 | Holm | |
| 5,612,050 A | 3/1997 | Rowe et al. | |
| 5,648,265 A | 7/1997 | Epstein | |
| 5,651,397 A * | 7/1997 | Black et al. | 141/18 |
| 5,656,035 A | 8/1997 | Avoy | |
| 5,759,169 A | 6/1998 | Marx | |
| 5,759,171 A | 6/1998 | Coelho et al. | |
| 5,788,662 A | 8/1998 | Antanavich et al. | |
| 5,827,262 A | 10/1998 | Neftel et al. | |
| 5,901,883 A | 5/1999 | Ritsche | |
| 5,935,437 A | 8/1999 | Whitmore | |
| 5,971,956 A | 10/1999 | Epstein | |
| 5,989,215 A | 11/1999 | Delmotte et al. | |
| 6,063,297 A | 5/2000 | Antanavich et al. | |
| 6,223,786 B1 * | 5/2001 | Castellano | 141/2 |
| 6,253,804 B1 * | 7/2001 | Safabash | 141/97 |
| 6,474,369 B2 * | 11/2002 | Castellano | 141/9 |
| 2002/0007863 A1 * | 1/2002 | Both et al. | 141/2 |
| 2002/0124905 A1 * | 9/2002 | Draughn et al. | 141/25 |

* cited by examiner

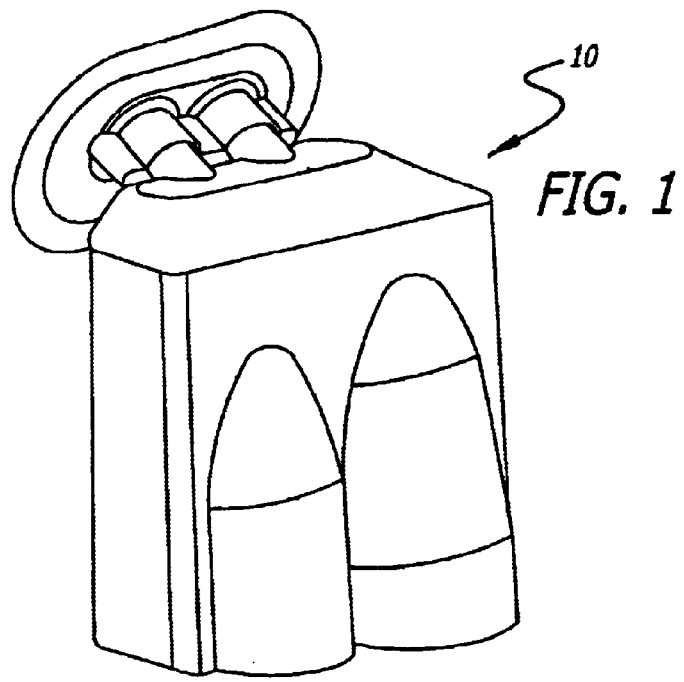
FIG. 1
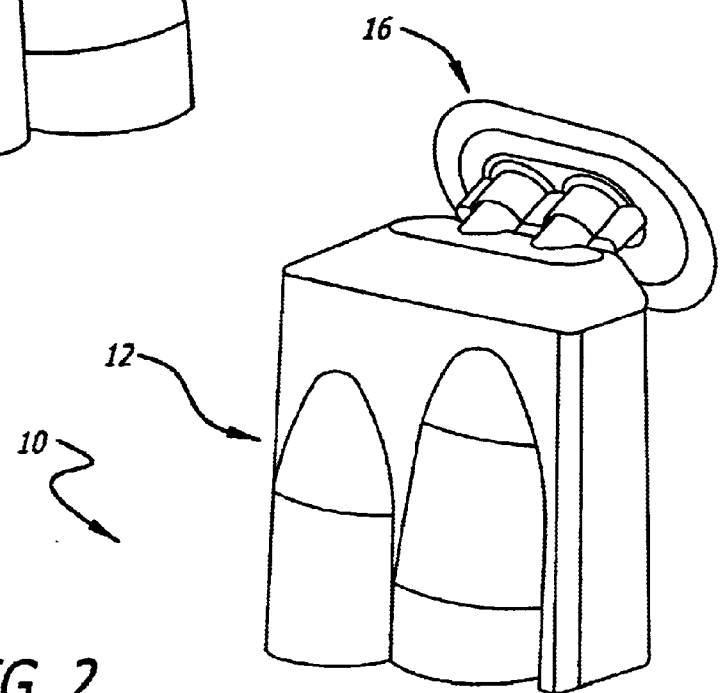
FIG. 2
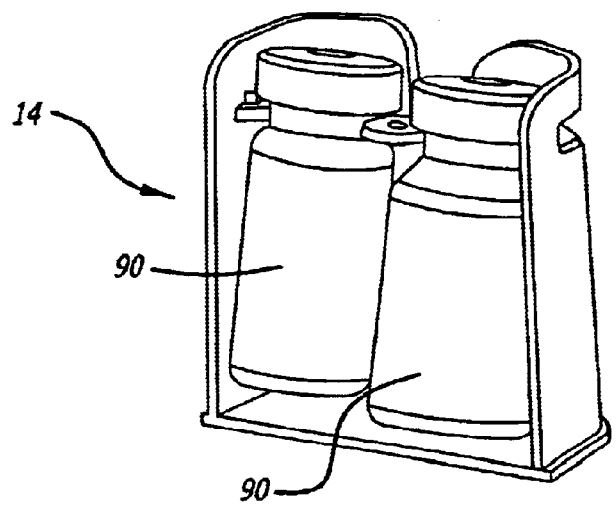

TILTING DIRECT DUAL FILLING DEVICE

BACKGROUND OF THE INVENTION

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first component containing fibrinogen and Factor XIII and, on the other hand, a second component which usually includes thrombin and calcium ions. Until May of 1998, when the FDA first approved such products, fibrin sealants were not commercially available in the US, therefore use of fibrin sealant was limited to supplies produced within the clinic, which are not subject to FDA control. Following FDA approval, the use of fibrin sealants has been increasing steadily. During use, the fibrinogen is capable of polymerizing and being cross-linked to form a solid fibrin clot when the components are mixed. The necessary additional factors to stimulate relevant portions of the natural blood coagulation cascade are suitably distributed between the fibrinogen and thrombin components.

Antanavich et al., U.S. Pat. No. 5,585,007, whose disclosure and references are hereby incorporated herein by reference in their entirety, provides an extensive discussion of the literature relating to fibrinogen sealant preparation (column 1, line 20 to column 4, line 62) and applicators (column 4 line 62 to column 5, line 14), as well as a bibliography, (columns 6–10) and is a helpful guide to the teachings of prior workers in the field.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging during the application process. These problems must be overcome in devising suitable applicators, methods of application, and devices suitable for filling the applicators.

A popular manually operable applicator for such two-component sealants employs a dual syringe construction wherein two syringes, connected by a yoke, each provide a reservoir for each of the components. In most prior devices, the sealant components are discharged-in separate streams and mixed externally of the applicator. Such applicators are similar in principle to household epoxy glue applicators commonly available in hardware stores.

Several devices and methods of filling biological glue applicators have been developed. For example, as taught in Epstein U.S. Pat. No. 5,266,877 and in our assignee's international application PCT/US98/07846, components of the sealant can be placed in separate compartments of a flat filler tray for transfer to an applicator. While these device have proven useful, several shortcoming have been identified. For example, although useful as a device to permit the reliable filling of a dual syringe applicator at the point of use, such filler trays are not suitable for external storage of the sealant components. In addition, the current filling process can be time consuming and it requires a significant degree of care to efficiently transfer the sealant to the applicator. Also, a small amount of sealant will be left in the tray, and is thus wasted. Furthermore the transfer of sealant components to the multiple storage containers of the applicator raises the possibility the sterility of the sealant will be compromised during component transfer.

Thus, there is a need for a device which can effectively deliver, in a sterile environment, multiple sealant components directly from their storage containers to a syringe applicator.

SUMMARY OF THE INVENTION

The present invention solves the problem of effectively delivering multiple sealant components directly from commercially available or standardized storage containers to an applicator while allowing the use of the entire fill device within a sterile field.

In one aspect, the invention provides a filling device capable of filling a material applicator and comprises a hood defining at least one receiving aperture, an applicator interface in communication with the hood and having at least one filling port formed thereon, at least one transfer conduit in communication with the at least one filling port, at least one withdrawal cannula located within the receiving aperture and in communication with the at least one transfer conduit, and a container support device capable of receiving and supporting at least one material container in an upright tilted position within the receiving aperture. The hood may include at least one engaging surface and at least one displacement recess.

In another embodiment, the present invention is directed to a filling device for simultaneously filling at least two material reservoirs of a material applicator. The filling device comprises a hood defining a receiving aperture and having an engaging surface and at least one displacement recess formed therein. An applicator interface is in communication with the hood and includes at least two filling ports formed thereon. At least two transfer conduits are in communication with the at least two filling ports and with at least two withdrawal cannulas located within the receiving aperture. A container support device capable of receiving and supporting at least two material containers in an upright position within the hood is included. The container support device includes at least one biasing member capable of engaging the engaging surface of the hood, wherein the biasing member is capable of biasing the at least two material containers to an upright tilted position within the hood.

In yet another aspect of the present invention, another filling device capable of filling at least two material reservoirs of a syringe applicator is disclosed. The filling device of the present embodiment comprises a hood defining at least one receiving aperture having an engaging surface and a displacement recess formed therein. An applicator interface is in located on the hood and includes at least two filling ports capable of sealably engaging the syringe applicator. At least two transfer conduits in communication with the at least two filling ports and the at least two withdrawal cannulas are located within the receiving aperture. A container support device capable of receiving and supporting at least two material containers in an upright position within the hood is provided. The container support device is capable of sealably engaging the hood. In addition, a biasing member is positioned on the container support device. The biasing member is capable of engaging the engaging surface formed on the hood and may bias the at least one material container to an upright tilted position.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein:

FIG. 1 shows a perspective view of the direct dual filing device of the present invention.

FIG. 2 shows a perspective view of the direct dual filing device of the present invention wherein the hood is displaced from the container support device.

DETAILED DESCRIPTION OF THE INVENTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

The tilting direct dual filling device of the present invention is used in conjunction with a multiple component applicator to dispense a multiple component fluid to a work surface. Those skilled in the art will appreciate that the present invention is particularly well suited to dispense a multiple component tissue sealant capable of effecting hemostasis or achieving other therapeutic results.

The tilting direct dual filling device of the present invention is designed to permit the-withdrawal by an applicator of a fluid from at least one commercially available fluid container. Those skilled in the art will appreciate that the present invention is adapted to functionally couple to a variety of applicators, including, for example, syringe-type applicators such as the DUPLOJECT™ syringe-type applicator manufactured by the Baxter Corporation. The present invention permits the controlled withdrawal of fluid from the fluid container and filling of at least one material reservoir contained in or in communication with the applicator. Furthermore, the tilting direct dual filling device of the present invention may permit the use and transport of commercially available component containers within a sterile environment. It is anticipated as being within the scope of the present invention to produce a tilting direct dual filling device capable of functionally coupling with a variety of applicators in a variety of sizes.

FIGS. 1 and 2 of the drawings show the tilting direct dual filling device 10 which comprises a hood 12 capable of engaging a container support device 14. The inventive device may be manufactured from a variety of materials, including, for example, polycarbonate, polystyrene, polypropylene, polytetrafluoroethylene, acrylonitrile butadiene-styrene, acrylic, or any other suitable material. In an alternate embodiment, at least the hood 12 of the present invention may be manufactured from a clear or visually transparent material. Those skilled in the art will appreciate that the inclusion of an enclosing hood permits the user to introduce an otherwise non-sterile container into a sterile environment. FIG. 2 shows one embodiment of the container support device 14 of the present invention supporting two material containers 90. Those skilled in the art will appreciate that the container support device 14 of the present invention may be easily adapted to support one or more material containers 90 within the hood 12.

Figure 3:
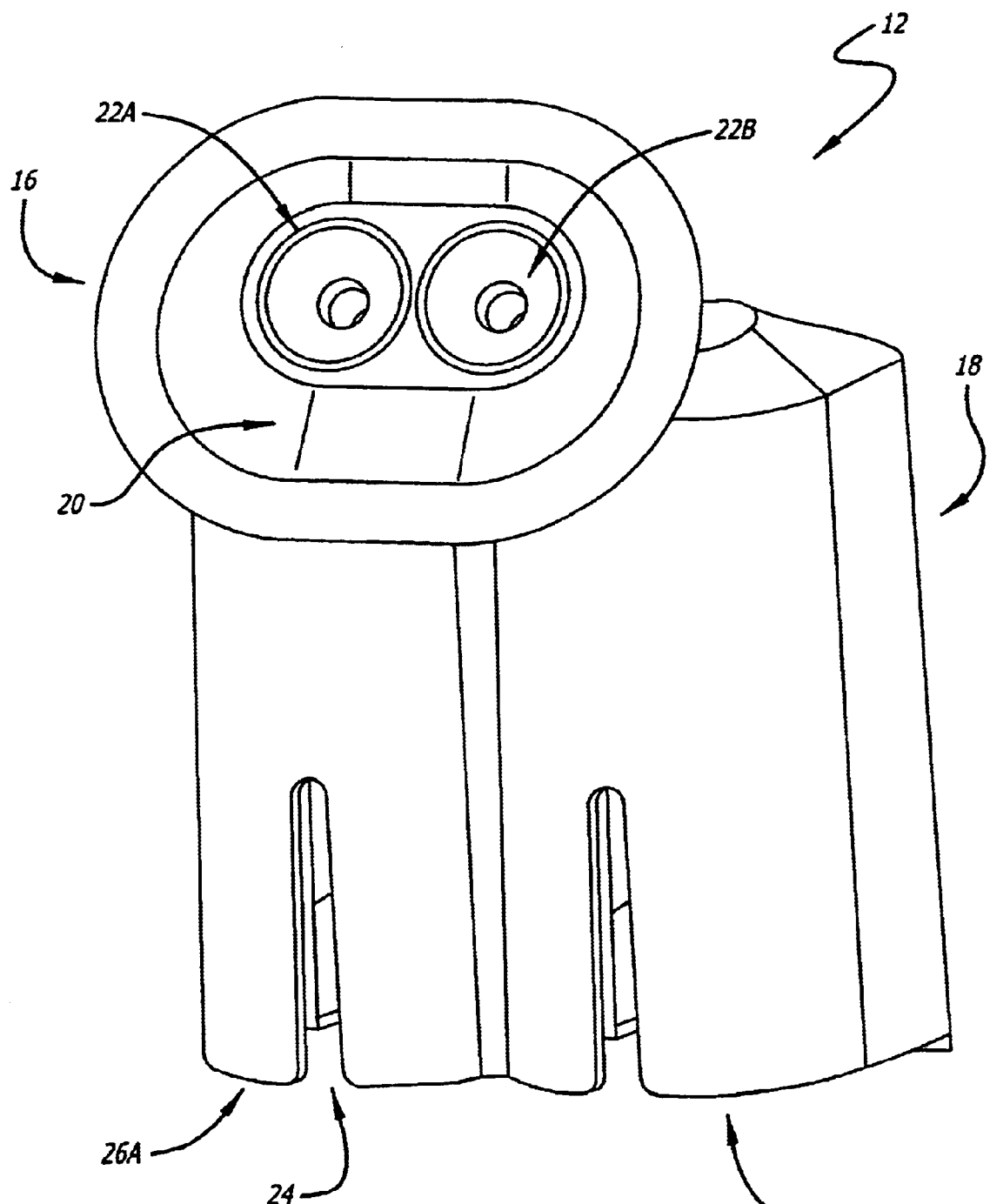
FIG. 3 shows a perspective view of the applicator interface attached to the hood of the present invention.

As shown in FIG. 3, the hood 12 includes an applicator interface 16 in communication with a hood body 18. As illustrated in FIG. 3, the applicator interface 16 comprises an applicator support structure 20 having at least a first and second filling port 22A and 22B, respectively, formed thereon. The first and second filling ports 22A and 22B, respectively, are capable of receiving an applicator therein. The hood body 18 defines a receiving aperture 24 sized to receive material containers of various sizes. In one exemplary embodiment, the receiving aperture 24 comprises a first container chamber 26A and a second container chamber 26B adapted to receiving individual material containers. Those skilled in the art will appreciate that the receiving aperture 24 may be formed in a variety of configurations, including, for example, a substantially oval or circular aperture, and may be capable of receiving one or more commercially available material containers therein.

Figure 4:
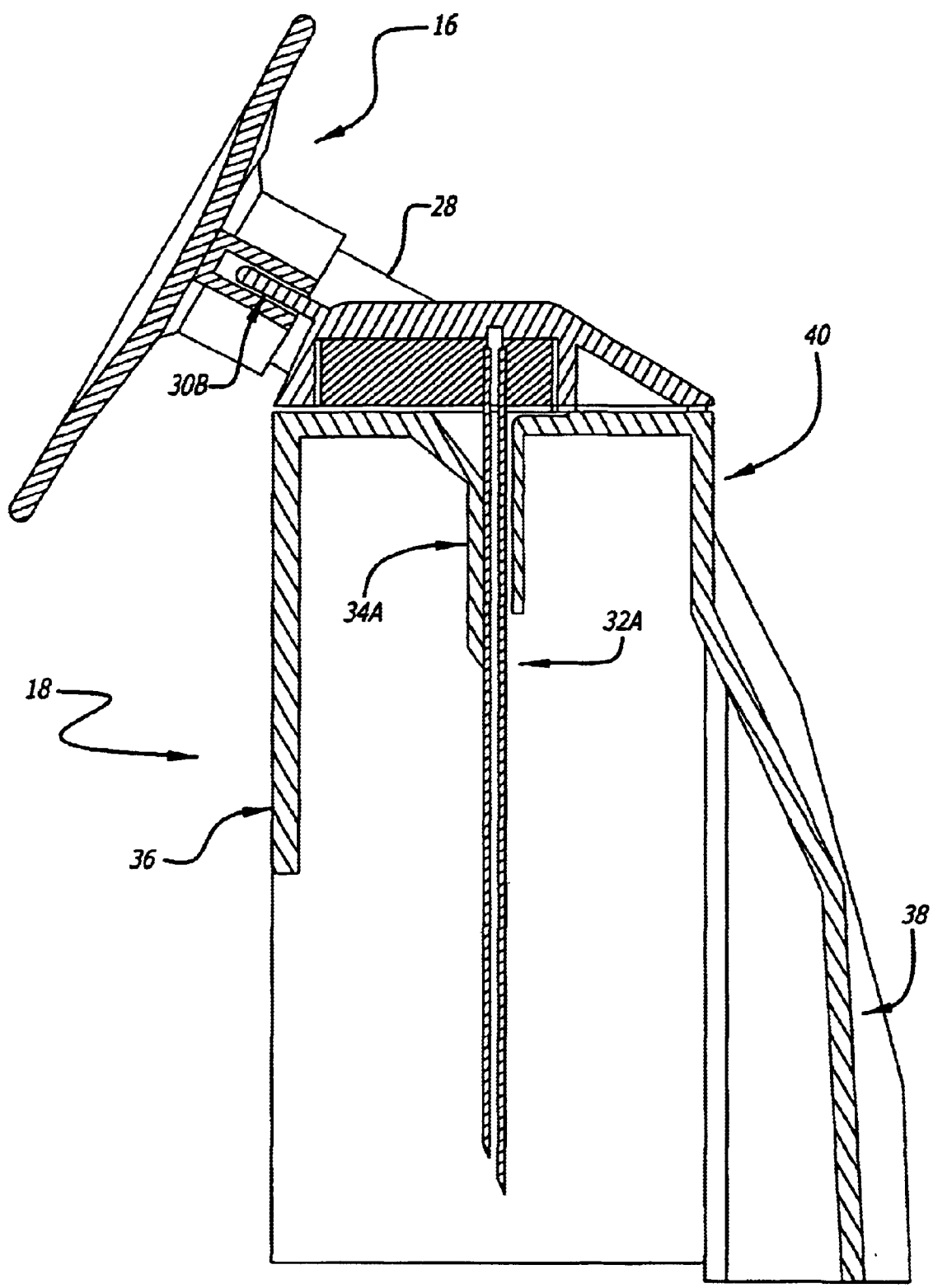
FIG. 4 shows a cross-sectional view of the hood of the present invention.
Figure 5:
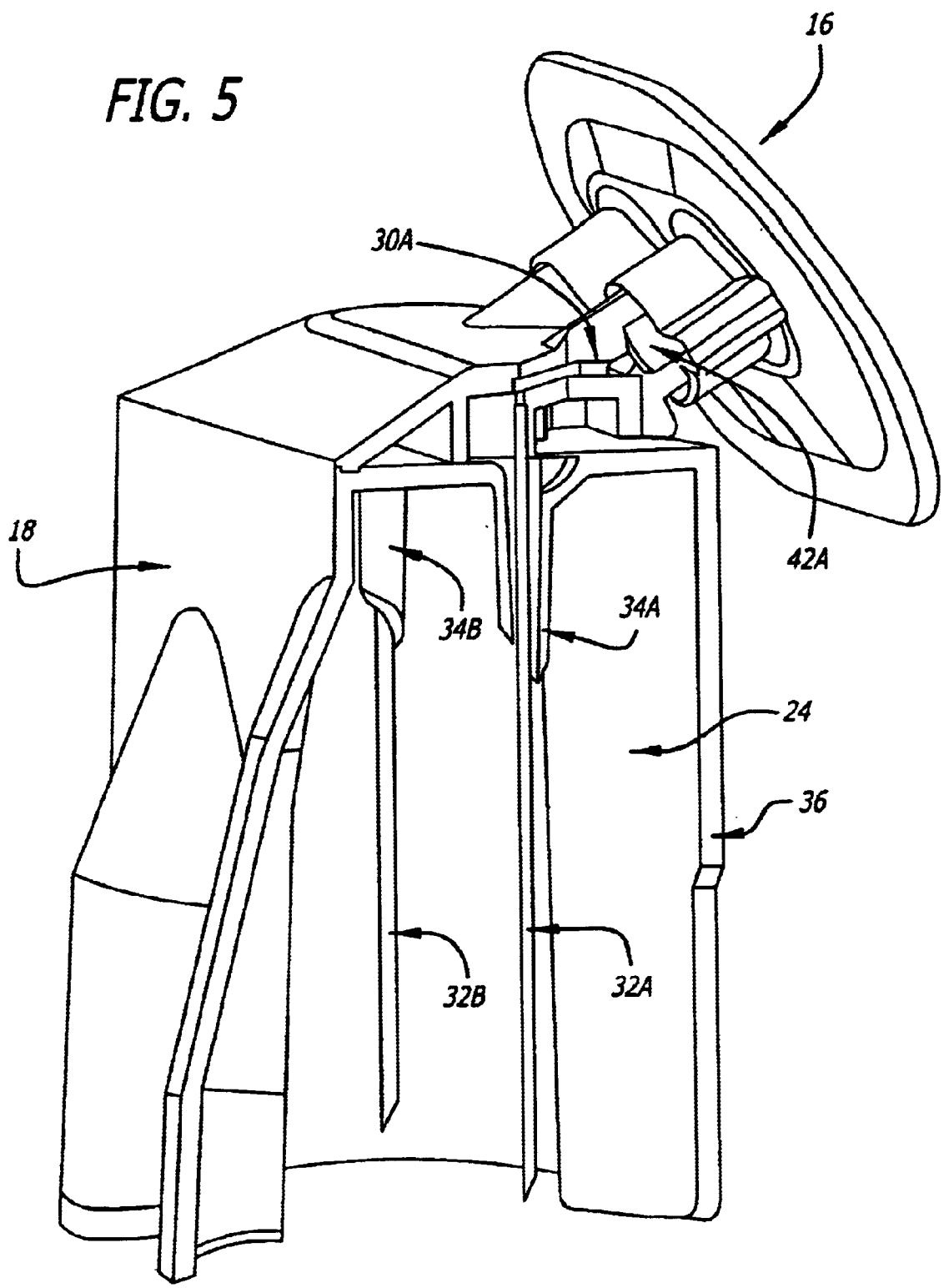
FIG. 5 shows the withdrawal cannulas positioned Within the hood of the present invention.

FIGS. 4 and 5 show the hood 12 of the present invention. The applicator interface 16 is capable of sealably engaging to an interface body 28 positioned on the hood body 18. In an illustrated embodiment, transfer conduits 30A, 30B are positioned within the interface body 28 and communicate with the filling ports 22A, 22B positioned on the applicator interface 16. Those skilled in the art will appreciate that the present invention permits the user to simultaneously fill separate reservoirs of an applicator from commercially available material containers without risk of cross contaminating the separated materials.

In one embodiment of the present invention, the applicator interface 16 is permanently attached to the interface body 28, wherein the filling ports 22A, 22B positioned on the applicator interface 16 are each capable of engaging an applicator. In another embodiment, the applicator interface 16 may be detachably coupled to the interface body 28, thereby permitting the user to easily adapt the present invention to interface with a variety of different applicators. For example, the present invention may include an applicator interface 16 capable of engaging a syringe-type applicator or an applicator interface 16 capable of engaging a spray applicator.

The first and second transfer lumens 30A, 30B communicate, respectively, with the first and second withdrawal cannulas 32A, 32B located within the receiving aperture 24 formed by the hood body 18. The first and second withdrawal cannulas 32A, 32B are preferably configured with pointed ends which have the ability to pierce the protective packaging found on standard medical fluid containers (not shown), including, without limitation, material bottles, vials, or bags. As shown in FIGS. 4 and 5, at least a first cannula support 34A is positioned proximate to the first withdrawal cannula 32A and is capable of providing support thereto. Similarly, a second cannula support 34B is positioned proximate to the second withdrawal cannula 32B and provides support thereto. The withdrawal cannulas 32A, 32B should have sufficient length to extract substantially all the fluid contained within a standard medical fluid container (not shown) positioned within the receiving aperture 24. In one embodiment, the withdrawal cannulas 32A, 328 are permanently attached to the first and second transfer lumens 30A and 30B. In an alternate embodiment, the withdrawal cannulas 32A, 32B may also have the ability to be detached from the first and second transfer conduits 30A and 30B for replacement. The withdrawal cannulas 32A, 32B may be of identical diameter or may differ in diameter to accommodate liquids having differing viscosities. Those skilled in the art will appreciate that the first and second withdrawal cannulas 32A and 32B, respectively, may be manufactured from a variety of materials including, for example, stainless steel or titanium.

Figure 7:
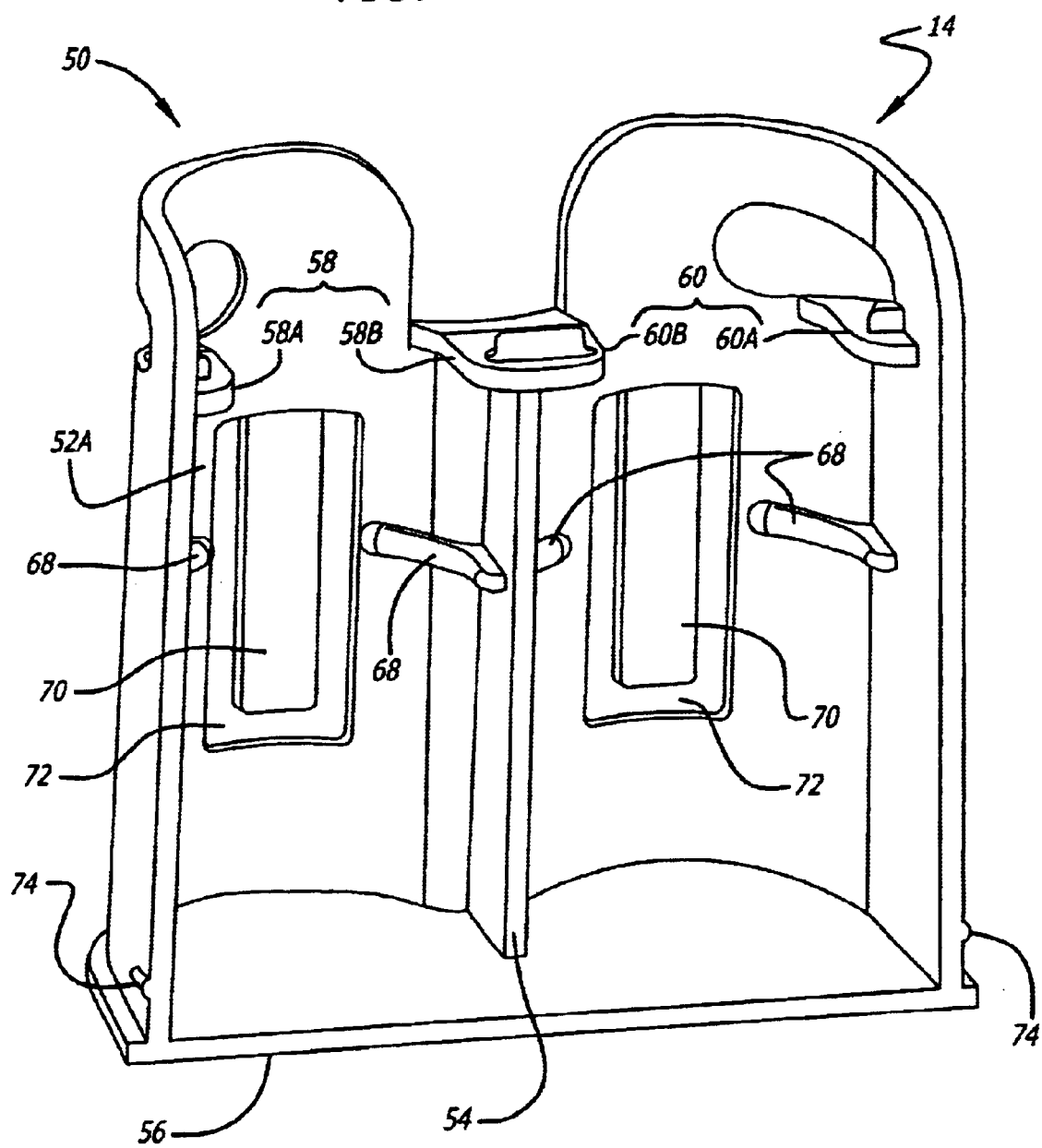
FIG. 7 shows a perspective view of the container support device of the present invention.

Referring again to FIG. 4 and 5, the receiving aperture 24 formed by the hood 12 comprises at least one engaging surface 36 and at least one displacement recess 38 formed on the hood planar surface 40. The engaging surface 36 is capable of engaging at least one biasing member (as shown in FIG. 7) disposed on the container support device 14 shown in FIG. 1. The at least one displacement recess 38 formed on the hood planar surface 40 is capable of receiving at least one material container in a tilted manner therein. In one embodiment, the hood 18 comprises a single displacement recess 38 formed within the receiving aperture 24. In another embodiment a plurality of displacement recesses 38 may be formed within the receiving aperture 24.

Figure 6:
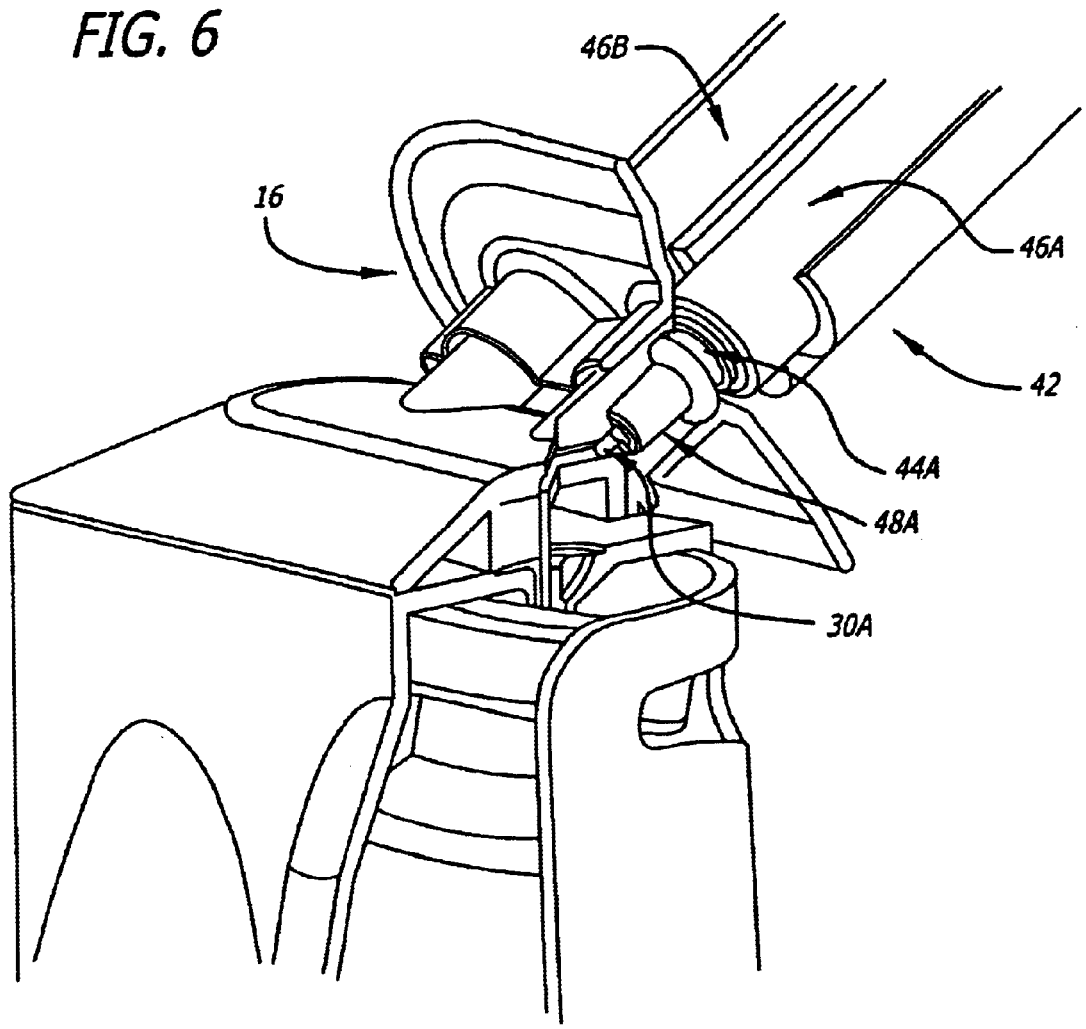
FIG. 6 shows an applicator positioned within the filling ports of the present invention.

FIG. 6 shows a syringe-type applicator 42 functionally coupled to the present invention. Generally, the applicator 42 will include at least two reservoirs capable of separately receiving and storing a plurality of fluids. As shown, the applicator 42 comprises a first applicator tip 44A in communication with a first applicator reservoir 46A and a second applicator tip 44B in communication with a second applicator reservoir 46B. The filling ports 22A and 22B include receiving channels 48A and 48B which are in communication with the transfer lumens 30A and 30B and are sized to sealably receive the applicator tips 44A and 44B. In one embodiment the receiving channels 48A and 48B are tapered to enhance the sealing engagement of the applicator tips 44A and 44B, although non-tapered configurations are also contemplated. In another embodiment, the receiving channels 48A and 48B may include a sealing o-ring (not shown) positioned therein to further ensure the sealing engagement of the applicator tips 48A and 48B.

The filling device 10 of the present invention utilizes a container support device 14 having a novel tilting mechanism to permit the withdrawal of substantial all fluid from a container supported thereby. FIGS. 7–10 show various views of the container support device 14 and the elements thereof in detail. As shown in FIG. 7, the container support device 14 comprises a support body 50 which defines at least a first container receiver 52A and a second container receiver 52B separated by at least one support member 54. A support base 56 is in communication with the support body 50 and the at least one support member 54. The container receivers 52A and 52B are sized to receive a variety of commercially available material containers. At least a first container support 58 capable of engaging and supporting a material container may be located within the first container receiver 52A. As shown, the first container support 58 may comprise first and second portions 58A, 58B positioned on or coupled to the support body 50, the at least one support member 54, or both. Similarly, a second container support 60 capable of engaging and supporting a material container may be located within the second container receiver 52B. Like the first container support 58, the second container support 60 may comprise first and second portions 60A, 60B positioned on or in communication with the support body 50, the at least one support member 54, or both.

Figure 8:
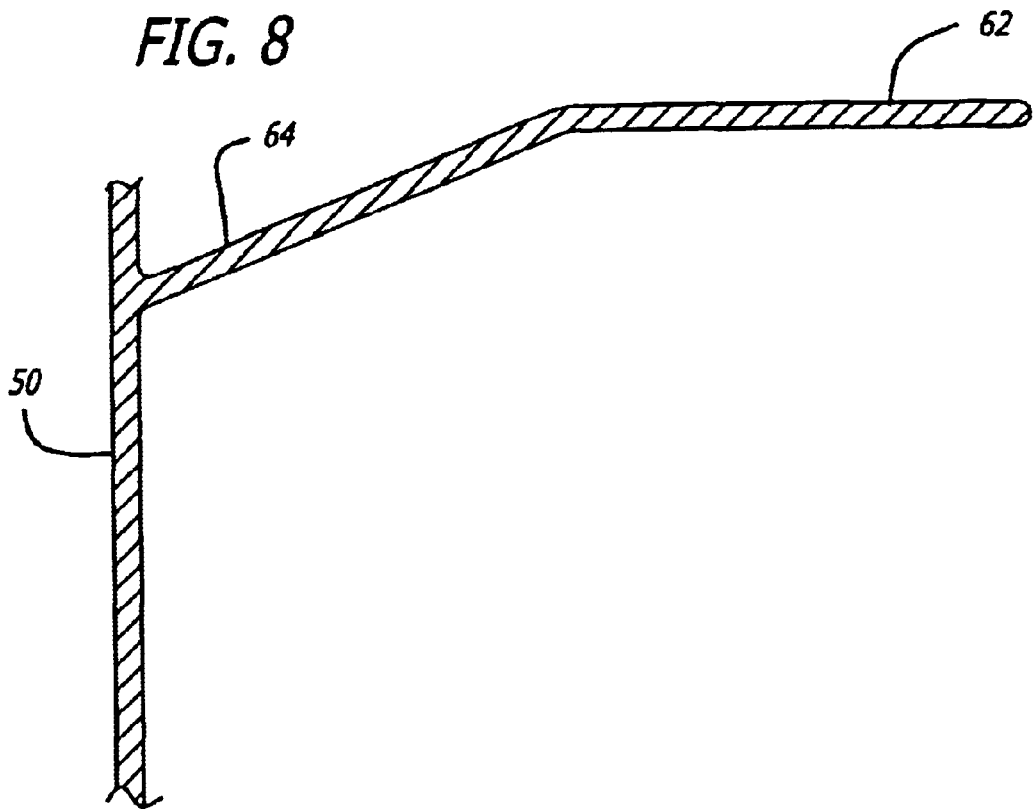
FIG. 8 shows a cross-sectional view of a container support of the present invention.
Figure 9:
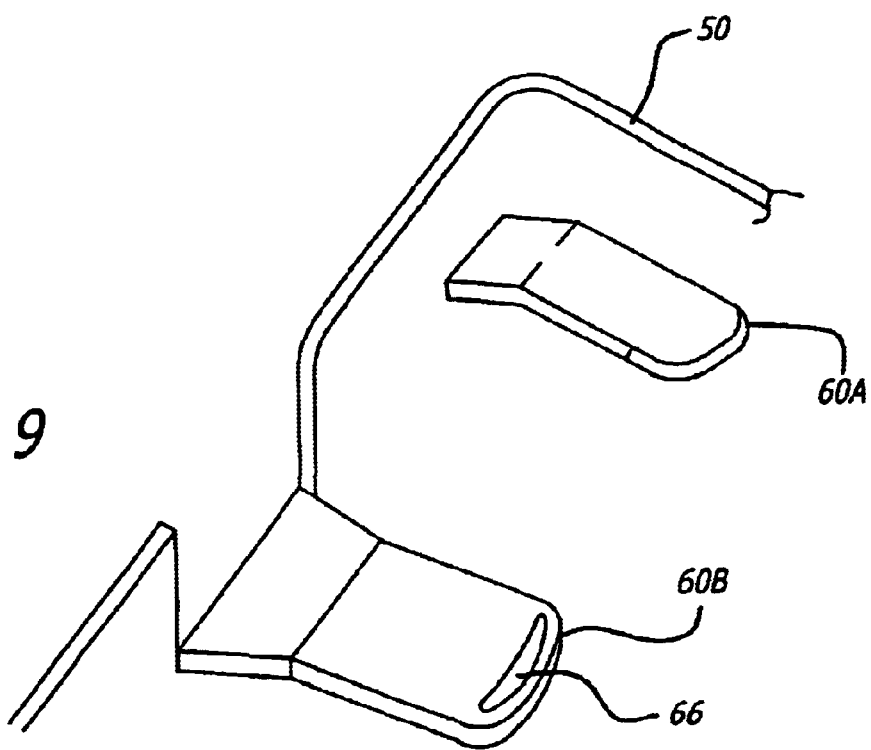
FIG. 9 shows a perspective view of the container supports coupled to the container support device of the present invention.

FIGS. 8 and 9 show various views of container support 58, 60 of the present invention. As shown in FIG. 8, the container supports 58, 60 include a first planer surface 62 in attached to an angled tilting surface 64, which couples the container support 58 to the support body 50. Those skilled in the art will appreciate that the angled tilting surface of the present invention permits a container supported thereby to be tilted while being supported by the container supports 58, 60. FIG. 9 shows a perspective view of the first and second portion 60A, 60B forming the second container support 60 positioned within the second container receiver 52B formed by the support body 50. A container retaining device 66 may be positioned on or attached to the container supports 58, 60. Exemplary retaining devices 66 include, for example, a ridge, bump, lock, recess, and indentation.

Figure 10:
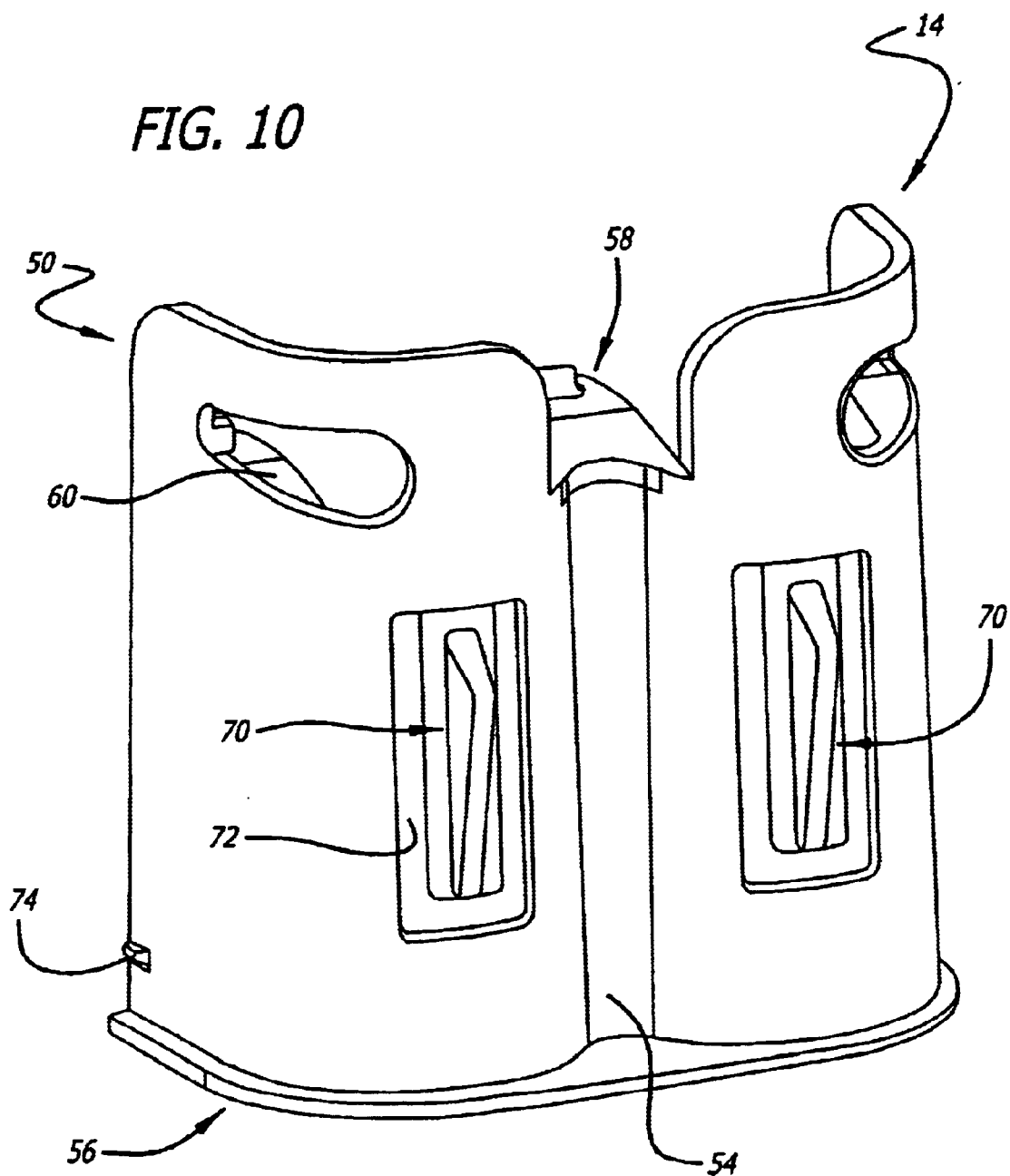
FIG. 10 shows an alternate view of the container support device of the present invention.

Referring again to FIG. 7, at least one auxiliary container support 68 may be located within the container receivers 52A, 52B. The at least one auxiliary container support 68 provides lateral support to at least one container being supported by the first and second container supports 58, 60. In addition, the at least one auxiliary container support 68 aids in aligning the container engaged by the first and second container supports 58, 60 with the first and second withdrawal cannulas 32A, 32B of the hood 12 of the present invention. As shown in FIG. 10, at least one biasing member 70 may be positioned with a biasing member recess 72 formed in the center of the support body 50 defining the container receivers 52A, 52B. The at least one biasing member 70 is attached to the support body 50 within a pivot (not shown), thereby permitting the inward movement of the at least one biasing member 70. Exemplary pivots include, without limitation, pins, rods, bearings, and flexible jointers. The support body 50 may include at least one coupling member 74 capable of engaging and retaining the hood 12 of the present invention. In an alternate embodiment, the container support member 14 of the present invention is capable of sealably engaging the hood 12 of the present invention thereby enabling the user to transport and use commercially available material containers in a sterile environment.

Figure 11:
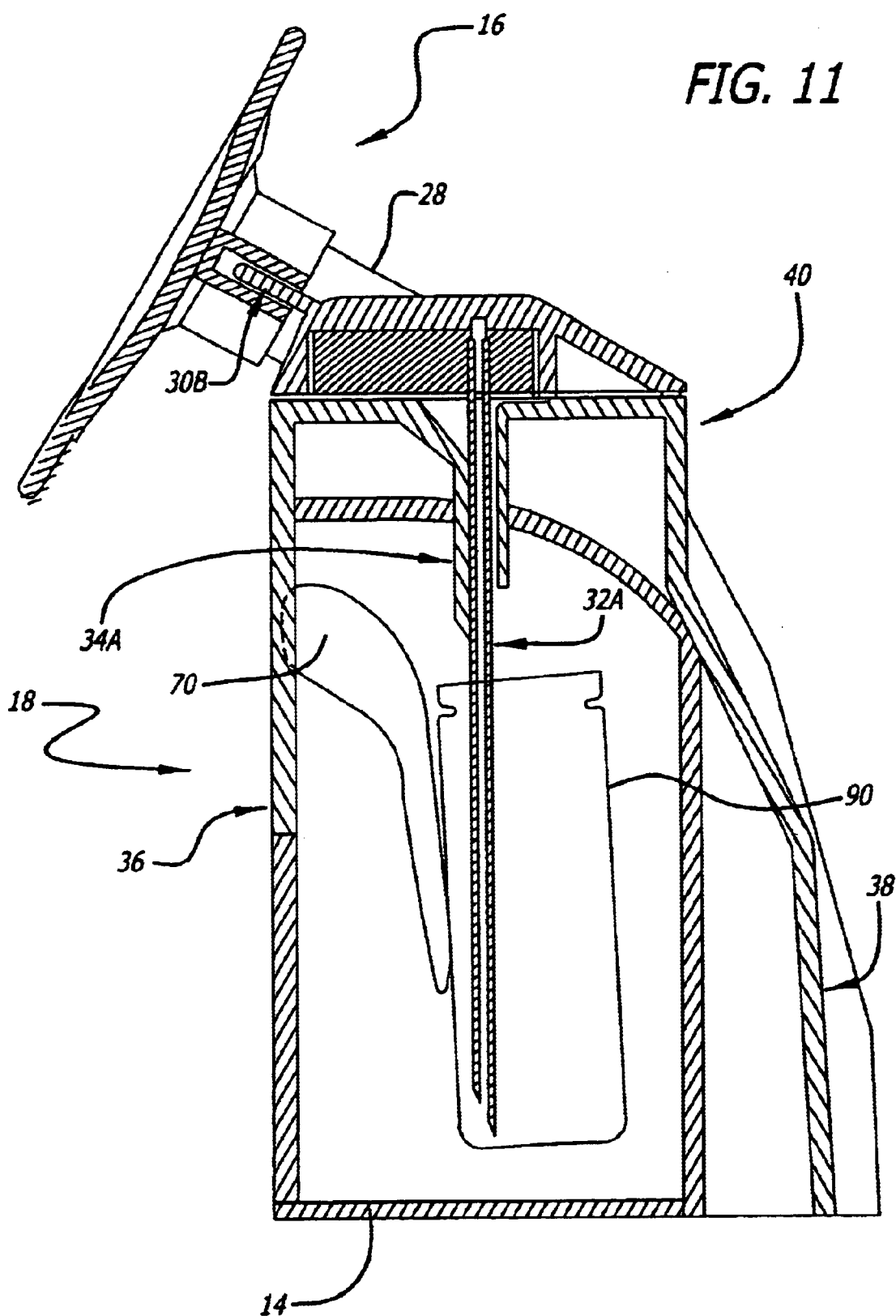
FIG. 11 shows a cross-sectional view of a material container positioned within the direct dual filling device of the present invention.

During use, one or more containers 90 may be positioned on the container support member 14. Thereafter, the container support device 14 is slidably inserted into the hood 12. As shown in FIG. 11, the at least an engaging surface 36 of the hood 12 engages and inwardly biases the at least one biasing member 70 of the container support device 14 into the container receivers 52A, 52B, thereby resulting in the container 90 tilting within the hood. Those skilled in the art will appreciate that the withdrawal cannulas 32A, 32B of the present invention are co-aligned with the lowest point of the material container 90 in a tilted position, thereby permitting the withdrawal of substantially all material from the material container 90.

Although only two containers 90 are depicted for use with the inventive filling device, adaptation can be easily made to allow the use of one or more containers 90 which can directly fill one or more reservoirs contained within the applicator. This adaptation can be accomplished by decreasing or expanding the housing member and adding or eliminating withdrawal cannulas, biasing members.

While illustrative embodiments of the invention have been described above, it is, of course, understood that various modifications will be apparent to those of ordinary skill in the art. Many such modifications are contemplated as being within the spirit and scope of the invention.

What is claimed:

1. An apparatus for filling a material applicator, comprising:
   a hood defining at least one receiving aperture, said hood comprising:
      at least one engaging surface located on said hood;
      at least one displacement recess formed within said at least one receiving aperture of said hood;
      an applicator interface having at least one filling port formed thereon coupled to said hood;
      at least one transfer conduit in fluid communication with said at least one filling port; and
      at least one withdrawal cannula located within said at least one receiving aperture and in fluid communication with said at least one transfer conduit; and
   a container support device capable of being received with said hood, said container support comprising:
      at least one support member capable of supporting at least one material container in an upright position within said receiving aperture; and
      at least one biasing member located on said container support device, said biasing member capable of biasing said at least one material container to an upright titled position.

2. The apparatus of claim 1, wherein said hood is made from at least one material selected from the group consisting of thermoplastic, plastic, polycarbonate, polystyrene, polypropylene, polytetrafluoroethylene, acrylonitrile butadiene-styrene, and acrylic.

3. The apparatus of claim 1 wherein said hood is manufactured from a see-through material.

4. The apparatus of claim 1 wherein said hood further comprises at least two displacement recesses formed on a common planar surface of said hood.

5. The apparatus of claim 1 wherein said at least one receiving aperture is capable of receiving at least one material container therein.

6. The apparatus member of claim 1 wherein said applicator interface is detachably coupled to said hood.

7. The apparatus of claim 1, wherein said at least one filling port is capable of sealably engaging at least one material applicator therein.

8. The apparatus of claim 1 wherein said at least one filling port further comprises at least one o-ring positioned therein.

9. The apparatus of claim 1 wherein said at least withdrawal cannula is permanently attached to said at least one transfer conduit.

10. The apparatus of claim 9, wherein said at least one withdrawal cannula comprises a pointed tip capable of piercing and sealably interfacing with said material container.

11. The apparatus of claim 1 wherein said at least one withdrawal cannula is detachably coupled to said at least one transfer conduit.

12. The apparatus of claim 1 wherein said at least one container support further comprises a first planar surface capable of supporting said material container in an upright position, and a second angled tilting surface capable of supporting said material container in an upright tilted position.

13. The apparatus of claim 1 wherein said at least one container support device further comprises a base member capable of engaging said hood.

14. The apparatus of claim 1 wherein said at least one biasing member is capable of engaging the at least one engaging surface located on said hood.

15. The apparatus of claim 14 wherein said at least one biasing member is capable biasing to an upright tilted position said material container supported by said at least container support device.

16. An apparatus for simultaneously filling at least two material reservoirs of a material applicator, comprising:
   a hood defining at least one receiving aperture, said hood comprising:
      at least one engaging surface formed on said hood;
      at least one displacement recess formed within said at least one receiving aperture of said hood
      an applicator interface having at least two filling ports formed thereon coupled to said hood;
      at least two transfer conduits in fluid communication with said at least two filling ports; and
      at least two withdrawal cannulas located within said receiving aperture and in communication with said at least two transfer conduits;
   a container support device capable of being received with said hood, said container support device comprising:
      at least one container support member capable of receiving and supporting at least two material containers in an upright position; and
   at least one biasing member located on said container support device capable of engaging said engaging surface of said hood, wherein said biasing member is capable of biasing said at least two material containers to an upright tilted position.

17. The apparatus of claim 16 wherein said at least two filling ports are capable of sealably engaging a multiple component syringe applicator.

18. An apparatus for simultaneously filling at least two material reservoirs of a syringe applicator, comprising:
   a hood defining at least one receiving aperture, said hood comprising:
      at least one engaging surface formed on said hood;
      at least one displacement recess formed within at least one receiving aperture;
      an applicator interface having at least two filling ports formed thereon coupled to said hood, wherein said at least two filling ports are capable of sealably engaging said syringe applicator;
      at least two transfer conduits formed in said hood, said at least two transfer conduits in communication with said at least two filling ports; and
      at least two withdrawal cannulas located within said receiving aperture and in communication with said at least two transfer conduits;
   a container support device capable of receiving and supporting at least two material containers in an upright position and capable of sealably engaging said hood, said container support device comprising:
      at least one biasing member located on said container support device capable of engaging said engaging surface, wherein said biasing member is capable of biasing said at least one material container to an upright tilted position.

* * * * *